United States Patent [19]
Simpson et al.

[11] Patent Number: 6,149,607
[45] Date of Patent: Nov. 21, 2000

[54] MULTIPLE SAMPLE BIOPSY DEVICE

[75] Inventors: Philip J. Simpson; David G. Matsuura, both of Escondido; John Kilcoyne, San Diego, all of Calif.

[73] Assignee: Endonetics, Inc., San Diego, Calif.

[21] Appl. No.: 09/128,882

[22] Filed: Aug. 4, 1998

[51] Int. Cl.[7] .................................................. A61B 10/00
[52] U.S. Cl. .......................... 600/567; 600/564; 606/167; 606/205; 606/207
[58] Field of Search ..................... 600/562, 564, 600/567; 606/52, 167, 170, 171, 174, 175, 205, 206, 207, 208, 209

[56] References Cited

U.S. PATENT DOCUMENTS

| | | | |
|---|---|---|---|
| 4,174,715 | 11/1979 | Hasson | 128/321 |
| 4,243,048 | 1/1981 | Griffin | 128/751 |
| 4,640,296 | 2/1987 | Schnepp-Pesch et al. | 128/754 |
| 4,887,612 | 12/1989 | Esser et al. | 128/751 |
| 5,052,402 | 10/1991 | Bencini et al. | 128/751 |
| 5,172,700 | 12/1992 | Bencini et al. | 128/751 |
| 5,195,533 | 3/1993 | Chin et al. | 128/754 |
| 5,251,641 | 10/1993 | Xavier | 128/754 |
| 5,320,627 | 6/1994 | Sorensen et al. | 606/167 |
| 5,373,854 | 12/1994 | Kolozsi | 128/749 |
| 5,385,570 | 1/1995 | Chin et al. | 606/170 |
| 5,415,182 | 5/1995 | Chin et al. | 128/754 |
| 5,538,008 | 7/1996 | Crowe | 128/751 |
| 5,542,432 | 8/1996 | Slater et al. | 128/751 |
| 5,562,102 | 10/1996 | Taylor | 128/751 |
| 5,573,008 | 11/1996 | Robinson et al. | 128/754 |
| 5,573,546 | 11/1996 | Nakao | 606/170 |
| 5,620,459 | 4/1997 | Lichtman | 606/174 |
| 5,638,827 | 6/1997 | Palmer et al. | 600/564 |
| 5,647,115 | 7/1997 | Slater et al. | 29/557 |
| 5,665,100 | 9/1997 | Yoon | 606/170 |
| 5,709,697 | 1/1998 | Ratcliff et al. | 606/167 |
| 5,762,069 | 6/1998 | Kelleher et al. | 128/751 |
| 5,776,075 | 7/1998 | Palmer | 600/564 |
| 5,797,957 | 8/1998 | Palmer et al. | 606/167 |
| 5,820,630 | 10/1998 | Lind | 606/208 |
| 5,843,000 | 10/1998 | Nishioka et al. | 600/566 |
| 5,871,453 | 2/1999 | Banik et al. | 600/564 |
| 5,895,361 | 4/1999 | Turturro | 600/562 |
| 5,919,202 | 7/1999 | Yoon | 606/170 |
| 5,922,002 | 7/1999 | Yoon | 606/170 |

FOREIGN PATENT DOCUMENTS

| | | |
|---|---|---|
| 2 479 680 | 4/1980 | France . |
| 1629038 A1 | 5/1988 | U.S.S.R. . |

*Primary Examiner*—Cary O'Connor
*Assistant Examiner*—Charles Marmor, II
*Attorney, Agent, or Firm*—Knobbe, Martens, Olsen and Bear, LLP

[57] ABSTRACT

A biopsy device for acquiring more than one tissue sample comprises an elongated, flexible actuator shaft which is slidable within an outer sleeve. A jaw portion is coupled to the actuator shaft and the outer sleeve in such a manner as to open when the shaft is moved in a first direction relative to the sleeve and close when the shaft is moved in a second direction relative to the sleeve.

38 Claims, 12 Drawing Sheets

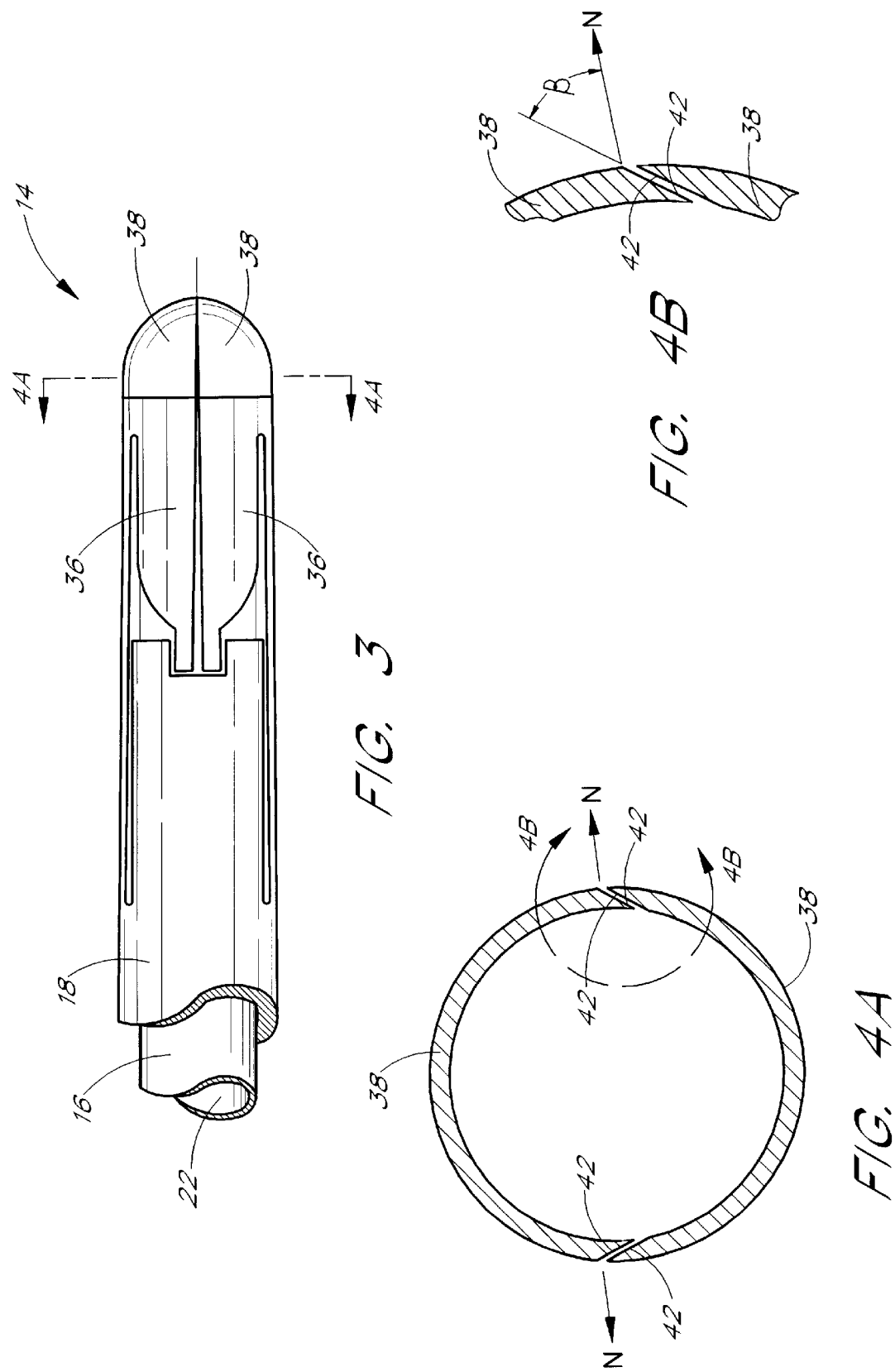

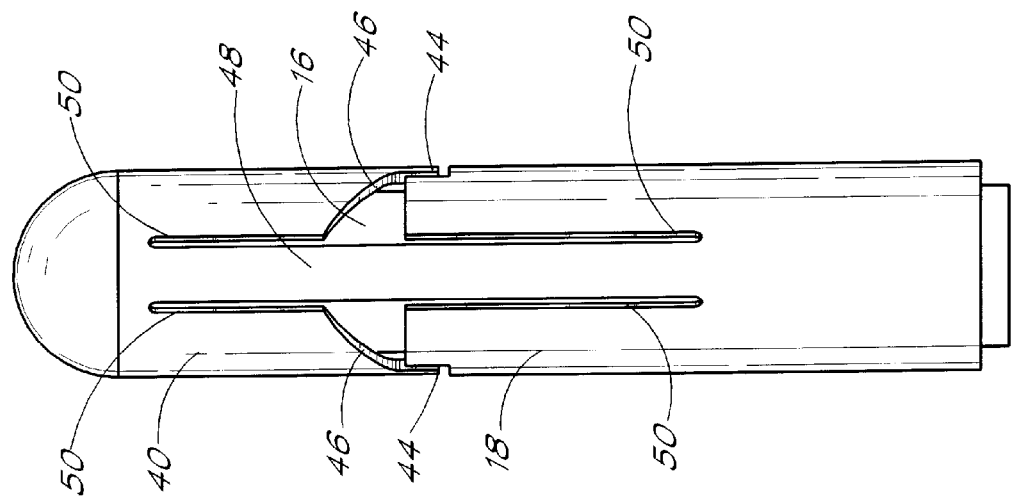
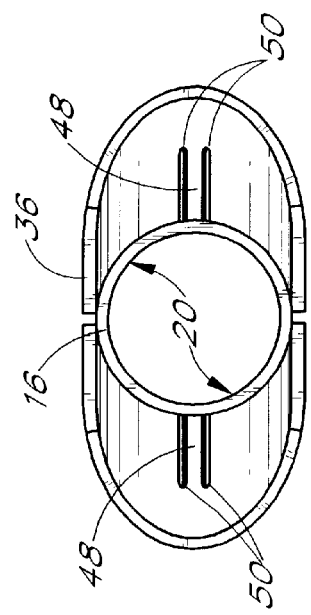

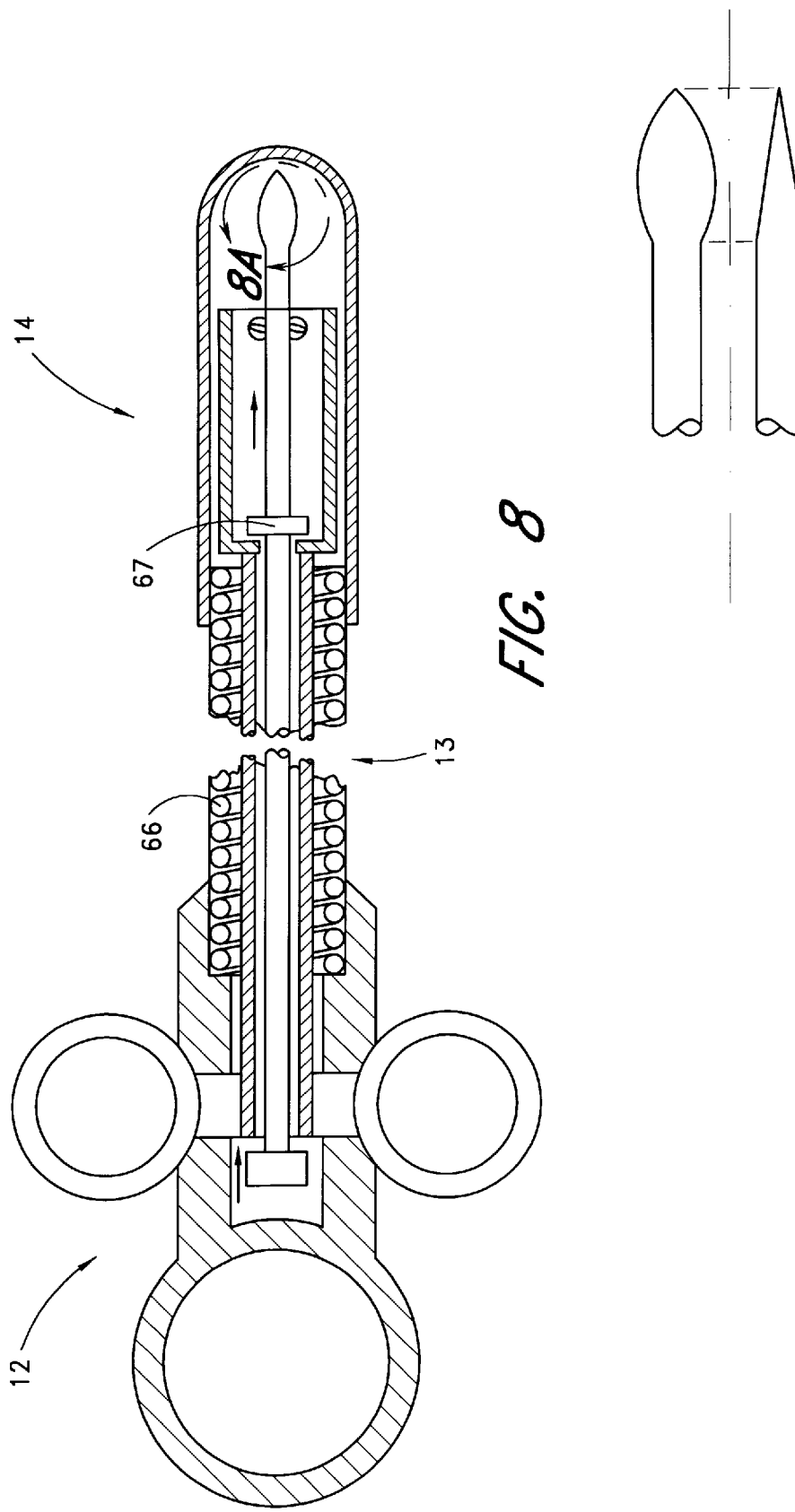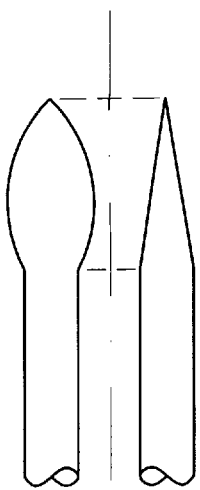

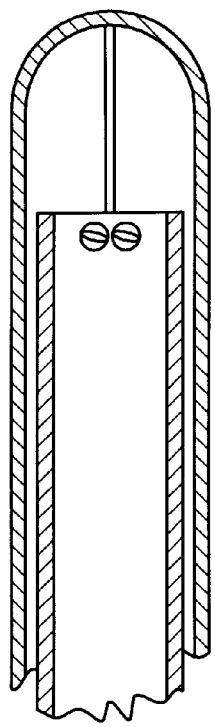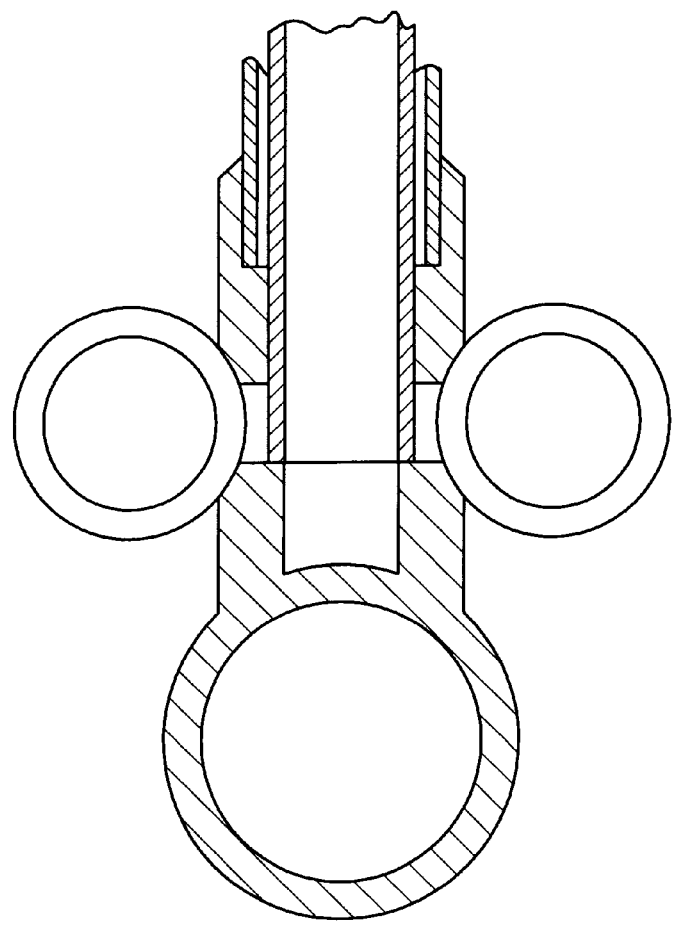
FIG. 11

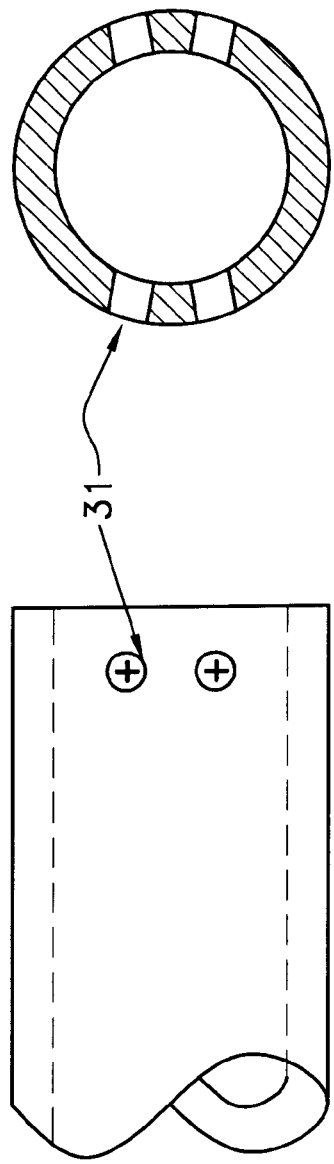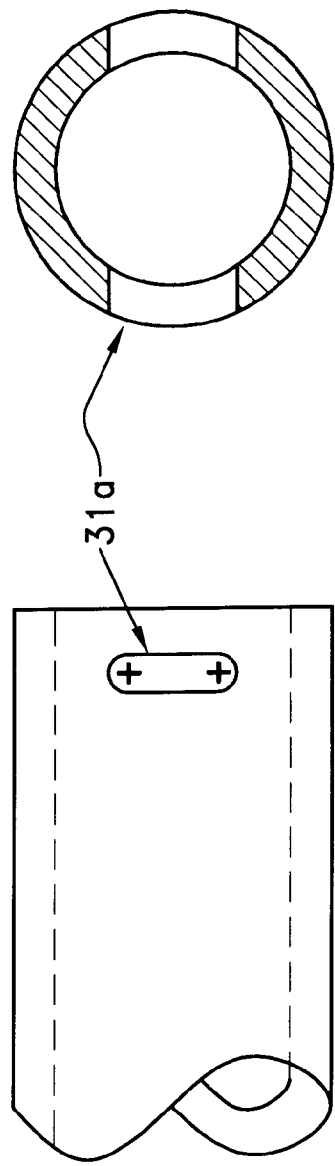

MULTIPLE SAMPLE BIOPSY DEVICE

BACKGROUND OF THE INVENTION

The present invention relates to medical instruments. More particularly, the present invention relates to devices for obtaining multiple internal tissue specimens from a patient.

Devices for the retrieval of tissue samples from within a patient are frequently used in conjunction with instruments such as flexible endoscopes. Endoscopes allow the visualization of internal structures of a patient by a clinician without the need for conventional exploratory surgery. When suspicious lesions or tissue masses are encountered during an endoscopic examination, it is helpful to excise and remove a small sample of the tissue for further analysis by a pathology laboratory.

Flexible biopsy forceps are often used to perform such tissue excision and Aretrieval. Conventional biopsy forceps may consist of an elongated, tightly-wound spring-coil body. The spring body has a control assembly at a proximal end and a jaw assembly at a distal end. The control assembly is typically a hand-operated push-pull mechanism that slides a control wire back and forth through a lumen of the spring-coil body. The control wire is usually attached to a pair of pivoting jaws in the jaw assembly. Pushing and pulling on the control wire opens and closes the jaws, respectively. Moreover, the jaws are typically joined to the body through a pivot pin which spans at least a portion of the lumen. Thus, the lumen is typically at least partially blocked or occluded by mechanical elements.

When used with a flexible endoscope, the forceps are inserted into the working channel of the endoscope and advanced distally. The tip of the endoscope is directed by the clinician using controls on the proximal end of the endoscope. Once the target site has been identified and is under direct vision, the forceps are advanced distally out of the working channel and the jaws are opened. Upon contact with the tissue, the jaws are tightly closed and the forceps are retracted slightly to cut and remove the tissue sample. Flexible biopsy forceps can also be used without an endoscope, as in, for instance, cardiac muscle biopsy procedures. In such procedures, the flexible biopsy forceps device is inserted through a blood vessel into a heart chamber, where a sample of cardiac tissue is excised.

With certain types of endoscopic examinations, it is necessary to take more than one tissue sample. For example, in surveying a region of a bowel for specific disease states, it is sometimes necessary to take between ten and twenty tissue samples. In these instances, the use of conventional biopsy forceps is time-consuming because the forceps must be withdrawn and re-inserted after each sample has been excised. Maintaining the tip of the endoscope in a steady position during the removal and re-insertion of the forceps is often a tedious and difficult task. Accordingly, the clinician's ability to keep track of which areas have been biopsied and which have not can be impaired. The impairment of this ability can result in a frustrating and lengthy procedure for both the patient and clinician.

There is, therefore, a need for a biopsy device capable of retrieving more than one tissue sample from within a patient. It is also preferable for the collected samples to be of a size comparable to those obtained from conventional biopsy forceps devices, and for such samples to be easily removed from the device. Moreover, it is desirable for the samples to be held in the order of collection for identification of the source of each sample. It is further desirable for such a device to be relatively inexpensive and easy to use.

SUMMARY OF THE INVENTION

There is provided in accordance with one aspect of the present invention a multiple sample biopsy device. The devise comprises an elongate body, having a proximal end and a distal end. A control is positioned on the proximal end of the body, and a cutter tip is positioned on the distal end of the body. The cutter tip comprises a tubular housing having a first and second opposing jaws intregally formed with the housing. In one embodiment, the body comprises an elongate flexible tube. In another embodiment, the body comprises a relatively laterally rigid or inflexible tubular body. The tubular body further comprises an actuator element extending axially therethrough, for connection to the cutter tip. Axial displacement of the actuator with respect to the tubular body causes the jaws to move between a first medial position and a second lateral position.

In accordance with another aspect of the present invention, there is provided a cutter tip for mounting on the distal end of a biopsy device. The tip comprises a tubular housing having a proximal end and a closed distal end. The distal end of the tubular housing is axially bisected into a first and second jaw portions by a proximally extending cut therethrough. A tubular sample collection container is axially movably positioned within the housing. A moveable connection is provided between the tubular sample container and the first and second jaws, such that axial displacement of the tubular sample collection container in a first direction causes the first and second jaws to move laterally away from each other, and axial displacement of the tubular sample container in a second axial direction causes the first and second jaws to advance medially towards each other. Preferably, each of the first and second jaws further comprises a flexural element extending between the tubular housing and the jaw.

In accordance with a further aspect of the present invention, there is provided a method of making a cutting tip for use in a medical instrument. The method comprises the steps of providing a tube having a closed distal end. The tube is thereafter cut from the closed distal end in a proximal direction to divide a portion of the tube into first and second opposing jaws. An actuator is positioned within the tube, and connected to a portion of each jaw such that axial displacement of the actuator produces lateral movement of at least one of the jaws.

Further features and advantages of the present invention will become apparent to those of skill in the art in view of the disclosure herein, when considered together with the attached drawings and claims.

BRIEF DESCRIPTION OF THE DRAWINGS

These and other features, aspects and advantages of the present invention will now be described with reference to the drawings of several currently preferred embodiments which are intended to illustrate and not to limit the present invention, and in which:

FIG. 3 is an enlarged side elevational view of the embodiment of FIG. 1;

FIG. 4A is a section through FIG. 3 taken along line 4A—4A;

FIG. 4B is an enlarged view of the area within line 4B—4B in FIG. 4A;

FIG. 5A is a top plan view of the embodiment of FIG. 1 illustrating a stopping edge and a straight-edged flexure member;

FIG. 6 is an end view of the embodiment of FIG. 1 with a hemispherical cap portion removed and the jaw members in an open position.

FIG. 8 is a cross-sectional side elevational view of a flexible shaft embodiment of the present invention, having a central lumen for auxiliary functions.

FIG. 11 is a cross-sectional side elevational view of a rigid shaft embodiment of the present invention.

FIG. 12 is a side elevational detail view of the distal end of the inner actuating sleeve or collection chamber.

FIG. 13 is an alternate embodiment of the detail view shown in FIG. 12.

DETAILED DESCRIPTION OF THE PREFERRED EMBODIMENTS

Figure 1:
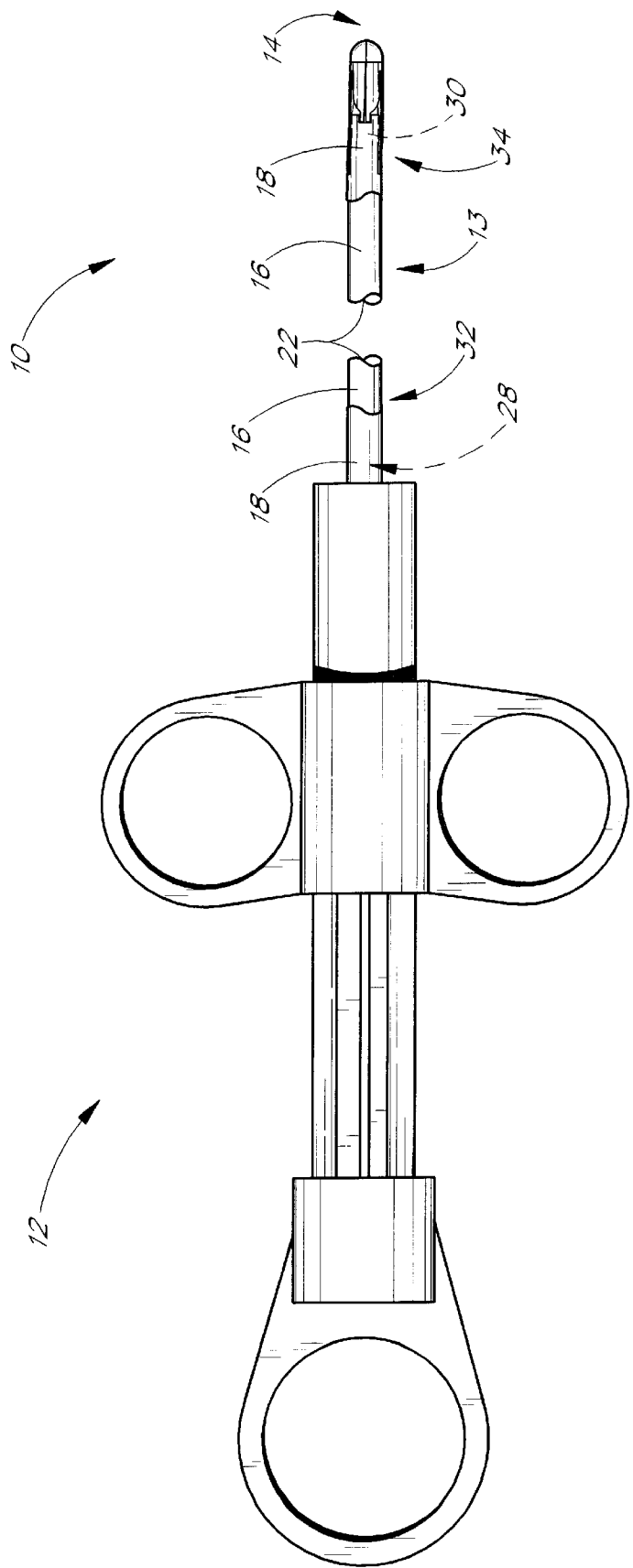
FIG. 1 is a side elevational view of an embodiment of a multiple sample biopsy device attached to an exemplary actuating handle.

Referring to FIG. 1, there is illustrated a multiple sample biopsy device 10 configured in accordance with certain aspects of the present invention. In general, the multiple sample biopsy device 10 comprises a proximal control or handle 12, an elongate body portion 13 and a cutting tip 14. As will be apparent to those of skill in the art in view of the disclosure herein, the cutting tip 14 of the present invention can readily be adapted for attachment to either a relatively rigid or relatively flexible body 13, of varying lengths and diameters, depending upon the desired clinical application.

For example, the concentric tubular structure disclosed in FIG. 1 will inherently produce a relatively rigid body which may be useful for laparoscopic, orthoscopic or other linear access applications as will be apparent to those of skill in the art.

Alternatively, the flexible body illustrated in FIGS. 7–10 may be used in conjunction with bronchoscopes, gastroscopes, sigmoidoscopes, colonoscopes, duodenoscopes, and other flexible introducer sheaths and equipment which are well known in the art. The flexible shaft embodiments are thus useful for advancement through any of a variety of tortuous pathways, including the GI tract, airways, and cardiovascular system, among other applications. Optimization of the cutting tip 14 of the present invention together with its flexible or rigid body 13 for any particular application can be readily accomplished by those of skill in the art in view of the disclosure herein.

As will become evident, the handle 12 used with the multiple sample biopsy device of the present invention need only move a first actuating element relative to a second actuating element to control the operation of a distal cutting tip on the device. The particular handle 12 illustrated herein is considered exemplary, and any of a wide variety of handle designs can be used. Further discussion of the handle is thus considered unnecessary.

Handle 12 (FIG. 1) is operatively linked to one or more cutting edges on the cutting tip 14, by way of a first actuating element such as actuator shaft 16, axially movably disposed with respect to a second actuating element such as an outer sleeve 18. Axial movement of the actuator shaft 16 in a first direction within the sleeve 18 closes cutting jaws on the cutting tip, allowing a sample of tissue to be severed from the patient and deposited within the collection chamber. Movement of the actuator shaft 16 in an opposite direction relative to the outer sleeve 18 in the illustrated configuration opens the jaws to allow the jaws to be advanced or otherwise repositioned to obtain a subsequent sample. Accordingly, the jaws open and close through a positive application of force and do not close purely as a result of a spring force or other biasing force.

Figure 2:
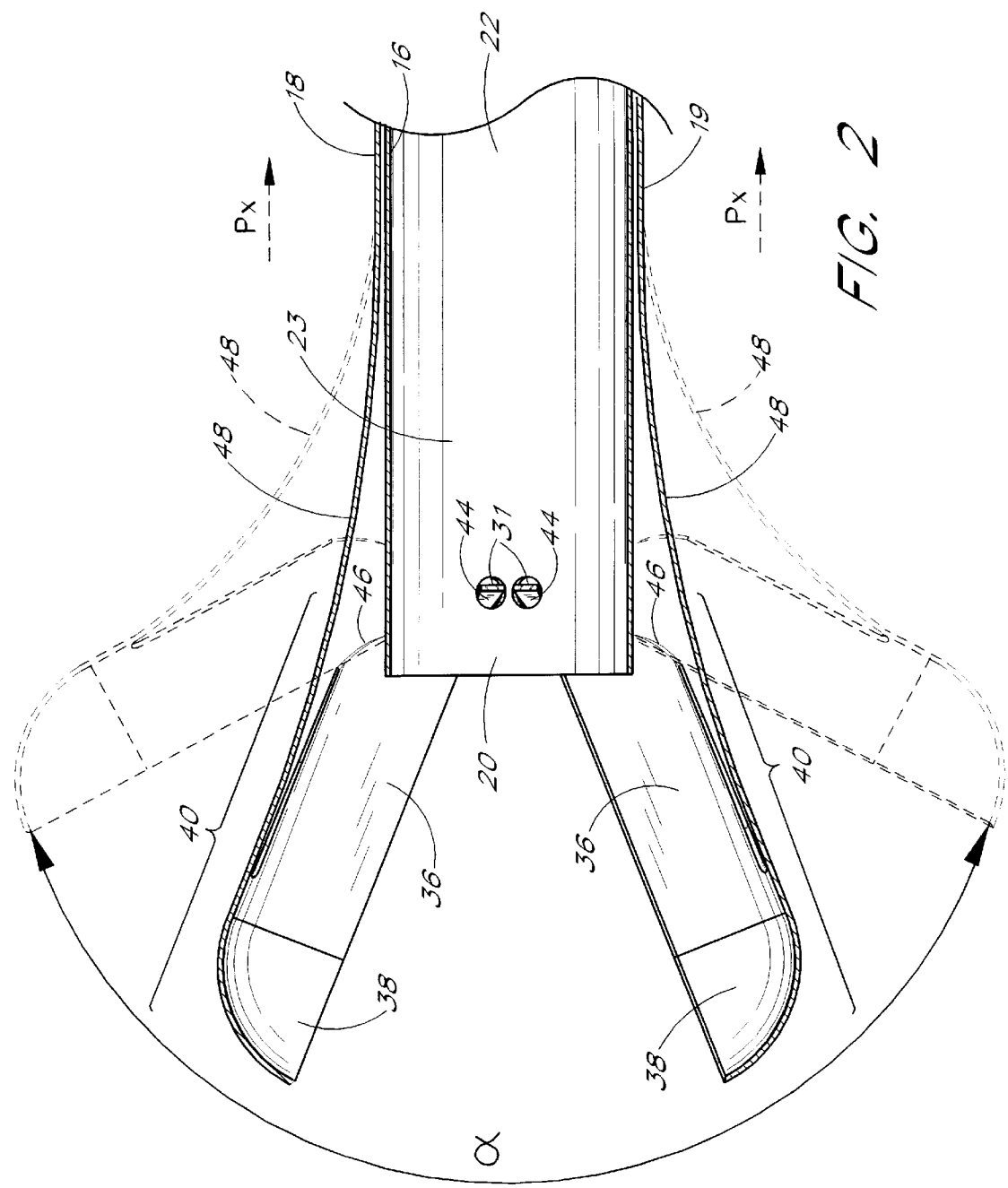
FIG. 2 is an enlarged cross-sectional side elevational view of the embodiment of FIG. 1 with a fully opened pair of jaws illustrated in phantom.

With reference to FIGS. 1–3, the illustrated actuator shaft 16 useful for rigid body embodiments will be described in detail. In one embodiment used for laparoscopic procedures such as biopsies of the ovaries or uterus, the shaft 16 is a thin-wall metal tube having an outside diameter of between about 2 mm and about 4 mm. In general, the wall thickness of actuator shaft 16 is chosen to optimize column strength and inside diameter while maintaining an acceptable O.D. for the desired procedure. Wall thicknesses generally within the range of from about 0.005" to about 0.010" may be used in a stainless steel construction.

Because the actuator shaft 16 extends from the control portion 12 (FIG. 1) to near the distal extremity of the device 10, the actuator shaft length varies according to its application. In general, the actuator shaft length can range from about 15 cm or less to about 50 cm or more depending upon the application. Any of the foregoing dimensions can be readily varied by persons of skill in the art, depending upon the intended use and performance characteristics of the device.

Although the actuator shaft 16 is illustrated in FIG. 1 as a tubular element, a solid rod having a round, rectangular or other cross-section may also be used. Alternative structures such as a spring coil tubular element may also be used, particularly in an embodiment in which the push/pull relationship between the shaft 16 and outer sleeve 18 are reversed from the illustrated embodiment so that cutting action is achieved by a distal, compressive force on the shaft 16. Polymeric materials may also be used, such as solid rods or extruded tubular elements, using any of a wide variety of relatively rigid plastics well known in the medical device field. In general, the first actuator such as actuating shaft 16 must simply have sufficient column strength and/or pulling strength to transmit sufficient axial force to the distal cutting tip to accomplish the clinical objectives of the biopsy tool.

In either the rigid shaft embodiments or the flexible shaft embodiments, discussed below, the actuator shaft 16 may be a solid structure, or be provided with a central lumen such as to permit the passage of biopsy samples in a proximal direction, or to accommodate additional implements or tools such as visualization and/or illumination devices. In addition, the central lumen in a hollow actuator shaft 16 may be utilized to permit passage of the device over a guidewire, such as in central or peripheral coronary vascular applications, or to permit infusion of fluids with or without medication, or to permit the aspiration of fluid samples.

The proximal portion 28 of the actuator shaft 16 is coupled to the control 12 to allow the clinician to control the desired axial translation of the actuator shaft 16 relative to the outer sleeve 18. In the illustrated embodiment, the actuator shaft 16 is coupled to the handle through a type of tensile-compressive connection (not shown). Any of a wide variety of joining techniques, such as mechanical interfit, solvent bonding, heat welding and the like, depending upon the construction materials, can be used at both the proximal and distal ends of the actuator shaft 16. Because the actuator shaft is connected to the handle portion in any suitable manner, further discussion of the connecting structure is considered unnecessary.

As shown in FIG. 2, the distal portion 30 of the illustrated actuator shaft 16 is provided with a plurality of jaw mounting apertures 31. In the illustrated embodiment, two pair, or a total of four, mounting apertures are provided. Alternatively, circumferentially extending slots (see FIG. 13) may be used. The illustrated jaw mounting apertures 31 are longitudinally aligned and arranged in pairs to permit pivotal attachment of each jaw member.

Although the mounting apertures 31 are illustrated as extending through the inner actuator shaft 16, for receiving radially inwardly extending tabs from the outer sleeve 18, any of a variety of alternative structures can be utilized to accomplish the hinging function for a cutting tip 14. For example, hinge pins or projections can extend radially outwardly from the actuator shaft 16, through corresponding apertures in the outer sleeve 18. Alternatively, any of a variety of flexible or pivotable hinge structures can be adapted for use in the present context, as will be apparent to those of skill in the art in view of the disclosure herein. In addition, although the hinge apertures 31 described above extend through a distal portion of the actuating shaft 16, analogous hinge mounting apertures will extend through the housing of a sample collection container in flexible shaft embodiments such as those illustrated in FIGS. 7–10 where the actuating shaft is provided with a separate sample collection container at its distal end.

As shown in FIG. 1, the outer sleeve 18, which cooperates with the actuating shaft 16 to allow the manipulation of the cutting tip 14 also has a proximal portion 32 and a distal portion 34. In one embodiment used for procedures such as esophageal biopsy, the sleeve 18 is a thin-wall metal tube having an outside diameter of between about 0.090" and about 0.125". The inside diameter provides sufficient clearance for a sliding fit with the actuator shaft 16 in the rigid shaft embodiment. The sleeve 18 also has a wall thickness between about 0.005" and about 0.010".

The outer sleeve 18 also extends from the control portion to nearly the distal extremity of the device 10. Accordingly, the outer sleeve length varies according to its application.

In one embodiment, the proximal portion 28 of the outer sleeve 18 desirably extends to the handle portion 12 and is coupled thereto such that the inner actuating shaft 16 can translate therein. The distal portion extends substantially to the proximal extremity of the cutter tip 14 in some embodiments. In the embodiment illustrated in FIG. 1, the jaw portions of cutter tip 14 are integrally formed with the outer sleeve 18.

With reference now to FIG. 2, the cutter tip 14 of the biopsy device 10 will be described in detail. As illustrated, in one embodiment, the cutter tip 14 is generally comprised of two half-cylindrical portions 36 which are combined with a corresponding pair of partially spherical cap portions 38 at their distal extremity. The jaw members 40 may be manufactured by forming a hemispherical cap 38 on the distal extremity of the cylindrical outer sleeve 18 or short cylindrical segment in a flexible shaft embodiment. The hemispherical cap and cylindrical sleeve are then axially bisected by laser cutting or any of a variety of other conventional cutting techniques. Alternatively, the cap can be soldered, bonded, brazed, or welded in any suitable manner to affix it to the distal extremity of outer sleeve 18. Additionally, where the outer sleeve 18 is molded or extruded of a suitable polymer, the cap 38 can be formed unitarily with or thermally bonded, soldered, solvent bonded, etc. to the balance of the outer sleeve.

As further illustrated in FIGS. 4a and 4b, the illustrated first and second jaw members 40 are provided with mating cutting edges 42. To form the complementary pair of cutting edges 42, an axially extending cut is made through both side walls of the jaw portion 14 from the distal end (i.e., through the cap 38). The longitudinal cut extends proximally for a desired distance. In the illustrated embodiment, the longitudinal cut extends from the distal extremity (i.e., the cap 38) for approximately the axial length of the jaw 40. In general, the jaw 40 can vary in axial length from about 0.1" to about 0.2" in the preferred endoscopic device disclosed herein. However, jaw lengths of as much as about 0.75" or greater can be used for larger diameter tools, as will be apparent to those of skill in the art.

As illustrated in FIGS. 4A and 4B, the cut in the illustrated embodiment is skewed relative to normal, N, by an angle β, through at least the cap 38 of the cutting tip 14. By skewing the cut, two complimentary tissue biting edges are formed. an In one embodiment, the cut is skewed between about 40° and about 50° from normal. The cutting edges 42 help to reduce the compressive force necessary to cut through the tissue sample to ease the removal of the sample from the patient. As will be recognized by those of skill in the art, the edges may also be bluntly formed such as by a normal cut relative to the surface of the hemispherical portion or the cylindrical sidewalls.

As best shown in FIG. 2, the proximal end of each jaw member 40 has a pair of inwardly extending, substantially opposing mounting tabs 44. The tabs 44 act as pivot points in the holes 31 located in the actuator shaft 16. Accordingly, the linear distance between the distal extremity of the jaw members 40 and the tabs 44 define the radius for the arc of travel for each jaw member when opening and closing. In an embodiment designed for procedures such as esophageal, colonic or gastric biopsy, the distance is between about 0.150" and about 0.170".

In the illustrated embodiment, the mounting tabs 44 are aligned with a corresponding pair of jaw mounting apertures 31. By positioning these tabs 44 on opposing sides of each jaw member 40, the jaw member 40 may be securely pivotably mounted to the remainder of the biopsy device. The length of each tab 44 in the radial direction is generally not substantially greater than the wall thickness of the actuator shaft 16, so that the sample collection chamber in the distal portion of the device remains substantially unobstructed.

With reference now to FIGS. 2 and 5A–5D, various cut patterns for forming the cutter tip 14 are shown. In its simplest form, the jaws 40, flexure members 48 and outer tubular housing 19 of the cutter tip 14 are formed from a single capped tubular element. The foregoing components are formed by laser cutting or otherwise cutting or etching the tubular blank in a patterned fashion such as that illustrated in FIGS. 5A–D. Alternatively, the jaws and collection chamber can be formed by a stamping operation such as that known as deep drawing.

Figure 5B:
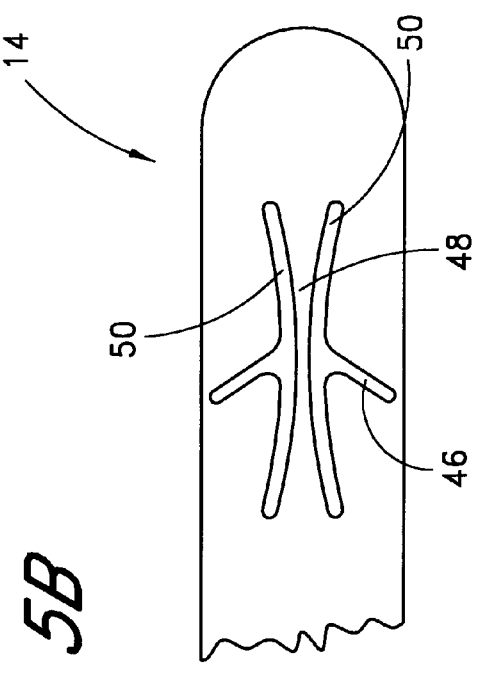
FIGS. 5B–5D are top plan views of additional embodiments of the cutting tip modified to reduce or redistribute stress in and around the flexure member.
Figure 5C:
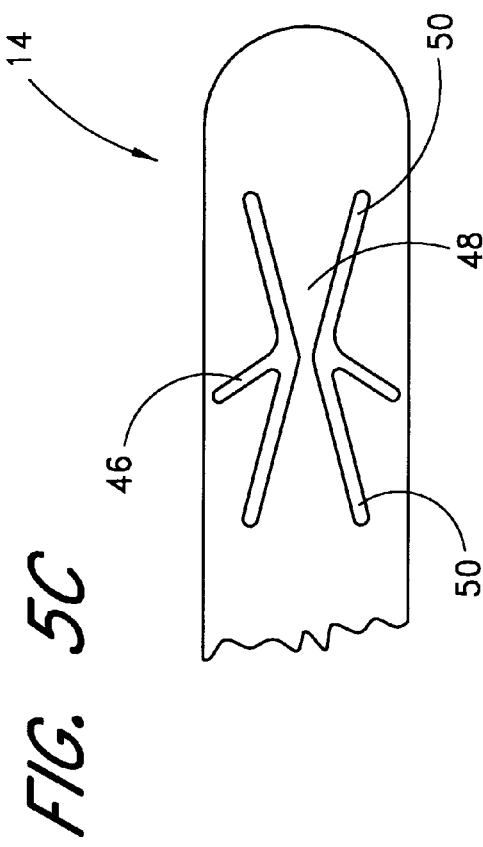

A stopping edge 46 is formed on the proximal end of each jaw member 40. In the illustrated embodiment, the stopping edge 46 is arcuate, as shown in FIGS. 5A–5C; however, as will be recognized by one of skill in the art, the stopping edge 46 can also have many other geometries. For instance, a properly located straight circumferential cut will also limit the fully opened angle of the jaw members 40.

The removal of material or other forming technique which results in the stopping edge contour provides the necessary clearance for the jaw member 40 to rotate relative to the tabs 44. The proximal extremity of the illustrated stopping edge 46 forms, in part, the tabs 44 when bent inward. Moreover, as a function of their geometry, the stopping edges 46 limit the range of motion possible for each associated jaw member 40. As illustrated in the embodiment of FIG. 2, the jaws have a maximum opening angle, α. When the stopping edge bottoms out against the outer wall of the cutter tip housing, the full range of motion for the jaw members has been traversed. In one embodiment, the maximum angle, α, is about 120°. In other embodiments, α can range from about 90° to about 130°.

Any of a variety of alternative structures can be used to limit arcuate travel of the jaws, such as a pin or folded tab on one of the actuator shaft 16 (or collection chamber) or outer sleeve 18 which slides within a complementary slot on the other of the shaft 16 or sleeve 18. In one embodiment, the outer sleeve 18 in the area of cutter tip 14 is provided with one or two or more generally U-shaped cuts, with the parallel legs of the U preferably extending in the axial direction. The cuts may be made such as by laser cutting, etching, stamping, or other known technique. The material at the center of the U-shaped cut may be folded radially inwardly to produce a tab, which may extend through the distal portion 30 of actuator shaft 16 in between a proximal and distal edge such as may be formed on either side of a complementary opening. The distance in the axial direction between the proximal and distal edge will produce a limit on the axial travel of the outer sleeve 18 with respect to the actuator shaft 16. This will in turn produce a limit on the range of motion of the jaws as will be apparent to those of skill in the art in view of the disclosure herein. The resulting hard stops in the range of axial motion between the inner and outer tubes prevents over opening and over forceful closing of the jaws, which could result in damage to the pivot pins or other undesired consequences.

The stopping edges 46 also isolate a pair of flexural members 48 as the only structural connection between the jaw members 40 and the cutter tip housing 19 (which may be the distal portion of the outer sleeve 18 in a rigid body embodiment). The flexural members 48, therefore, are the flexible linkage between the jaw members 40 and the cutter tip housing 19 which allow the jaw members 40 to open and close relative to each other. A springy quality of the flexural members 48 tends to hold the jaw members 40 in a normally closed or semi-closed position; however, as will be recognized by one of skill in the art, the jaw members 40 can alternatively be configured to be biased in a normally open position.

When the inner actuating shaft 16 is moved distally relative to the outer sleeve 18, the tabs 44 are advanced distally along an axial path. The flexural members restrain the movement of a distal outside portion of the jaw member 40 and thereby a rotational opening moment is set up with the jaw portion 14: The jaw portion is, therefore, forced open. As will be appreciated, a corresponding proximal movement of the tabs 44 relative to the remainder of the cutter tip housing 19 creates a closing moment.

FIGS. 5A–5D illustrate different embodiments of the flexural members 48. In essence, the flexural members 48 are thin, axially extending strips of the material of cutter tip housing 19 which are coupled at a proximal end to the housing and at a distal end to the jaw member 40. The circumferential width of the flexural members 48 generally ranges from about 0.025" to about 0.035". While the illustrated embodiments utilize flexural members 48, as will be recognized by one of skill in the art, the flexural members could also be biased hinges, non-compressible straps, and the like.

In the illustrated embodiments, the flexural members 48, jaw members 40 and cutter tip housing 19 are advantageously formed from a single tubular member. Each flexural member 48 is preferably formed between two bilaterally symmetrical longitudinal cuts 50 of a desired length. The cuts 50 begin at a point proximal to the distal end of the cutter tip and extend proximally. In one embodiment, the cuts begin between about 0.050" and about 0.060" from the distal end of the outer sleeve 18 and extend proximally for between about 0.180" and about 0.200". In other embodiments, the cuts extend proximally between about 0.150" and about 0.250".

Figure 5D:
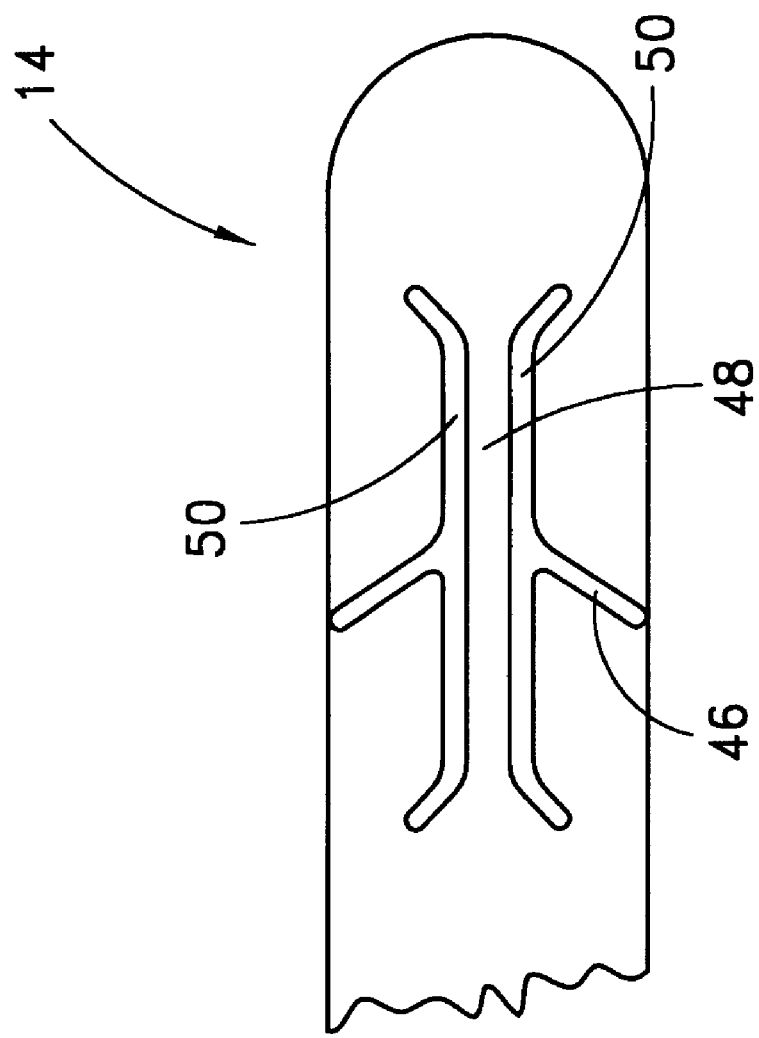

As illustrated, the mirror-image cuts 50 can be substantially linear in an axial direction (see FIG. 5A), crescent-shaped (see FIG. 5B) or variations on hour-glass shaped (see FIGS. 5C and 5D). The straight sides illustrated in FIG. 5A tend to create stress risers at the axial ends of the flexural member 48. The embodiments of FIGS. 5B–5D tend to more evenly distribute the bending stresses. The cuts 50 may conveniently be made by laser; however, various other forms of cutting, machining or molding are also contemplated.

By arranging the flexural members 48 radially as far as possible from the tabs 44, maximum closing force can be achieved in the jaw members 40. In addition, this location results in the arrangement of the flexural member 48 being substantially centralized between the tabs in a symmetrical fashion. Thus, a torsional stability results from the illustrated design because the resultant moment (i.e., the result of the two counteracting moments) created by the flexural member 48 is reduced. In addition, the longitudinal placement of the cuts determines the longitudinal placement of the flexural member. As will be appreciated, the longitudinal placement of the flexural member 48 relative to the tabs 44 impacts the opening and closing moments discussed above.

In some embodiments, the multiple sample biopsy device 10 can be made from several different components. Because the jaw members 40, the flexural members 48, and the outer sleeve 18 are advantageously a unitary structure in the illustrated embodiment, the outer sleeve 18 and the cap 38 should be made from a material which is hard enough to provide good biting surfaces (possibly sharpenable) for the jaw members 40, springy enough to provide the requisite flexing properties of the flexural members 48, rigid enough to function properly as the outer sleeve 18, and strong enough to withstand multiple sampling and the associated repeated flexing. Some presently preferred materials include, but are not limited to, stainless steel, and nitinol. Other metals, or any of a wide variety of polymeric materials well known in the medical device art may also be used. Other embodiments are also envisioned in which a plurality of materials are combined to form different components of a single device.

Figure 7:
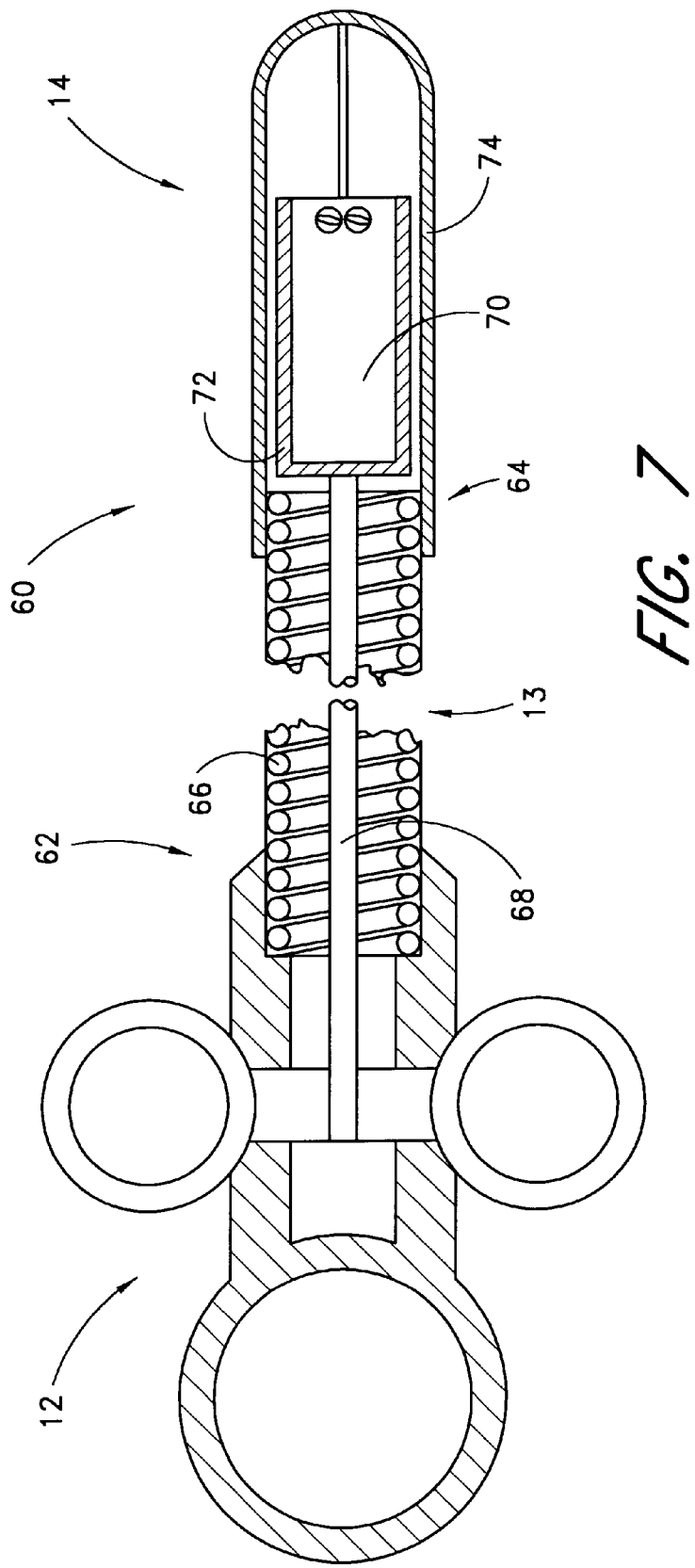
FIG. 7 is a cross-sectional side elevational view of a flexible shaft embodiment of the present invention.

Referring to FIG. 7, there is illustrated a flexible shaft biopsy device 60 in accordance with another aspect of the present invention. The flexible shaft biopsy device 60 generally comprises a proximal end 62, a distal end 64, and an elongate flexible body 13 extending therebetween. Proximal end 62 is provided with a control 12 as has been described. Distal end 64 is provided with a cutter tip 14 such as that previously disclosed herein.

The elongate flexible tubular body 13 comprises a first element 66 and a second element 68, which are laterally flexible and axially reciprocally moveable with respect to each other to translate movement from the proximal control 12 to the cutter tip 14. In the illustrated embodiment, the first element 66 comprises a flexible spring coil body as will be understood by those of skill in the flexible catheter arts. Depending upon the intended clinical application, the spring coil body may have an axial length within the range of from about 10 cm or less to as much as 300 cm or longer. The outside diameter may be optimized to suit the particular application, such as may be required by the inside diameter of the working channel or other introducer lumen through which the device 60 is to be inserted. In general, the outside diameter of the tubular body 66 will be no more than about 5 mm, and, preferably within the range of from about 1.8 mm to about 3.7 mm. The coil may comprise any of a variety of materials such as stainless steel, nitinol, or others known in the art. The wire may have a circular cross-section as illustrated, or rectangular or other cross-section depending upon the desired clinical performance.

The spring coil may be further provided with an outer and/or inner elastomeric sleeve such as an outer heat shrink tubing as is known in the art. In one embodiment, the heat shrink tubing comprises high density polyethylene having a wall thickness of about 0.002". Alternatively, an outer jacket may be provided on the spring coil body through any of a variety of techniques such as spraying, dipping, extrusion and the like.

The second element 68 in the illustrated embodiment comprises an elongate flexible pull/push wire. The cross-sectional configuration, diameter and material of the pull/push wire 68 is preferably selected to optimize the pulling and pushing characteristics necessary to impart sufficient cutting force to the cutting tip 14. In one embodiment, a round cross-section stainless steel wire having a diameter of about 0.015" and an axial length of about 60" has been found useful. The wire may have a constant diameter throughout, or may be tapered or stepped down from a larger diameter at the proximal end to a smaller diameter at the distal end depending upon the desired flexibility characteristics of the device.

The distal end of the pull wire 68 is connected to a sample collection chamber 70. The sample collection chamber 70 comprises a generally cylindrical wall 72, axially movably disposed within the housing 74 of cutting tip 14. The operation of the wall 72, outer housing 74 and cutting jaws on the cutting tip 14 may be in accordance with embodiments previously disclosed herein.

In a flexible shaft embodiment, the overall flexibility and maneuverability of the biopsy tool will be limited by the axial length of the cutting tip. Thus, the cutting tip is preferably maintained at a relatively short axial length, such as no more than about 2 cm and, preferably, no more than about 1.0 or 1.5 cm long. The axial length of the cylindrical wall 72 which defines sample collection chamber 70 will normally be less than the overall length of the cutting tip. The axial length of collection chamber 70 can be optimized in any particular embodiment, taking into account the desired volume for the collection chamber 70, as well as the maximum permissible length of the collection chamber 70 in view of the desired flexibility for any particular application.

Referring to FIG. 8, there is illustrated a further feature of the present invention, which may be adapted either to the rigid body or the flexible body embodiments of the multiple sample tissue biopsy device. In the illustrated embodiment, the actuator shaft 16 comprises an elongate tubular element such as a section of hypodermic tubing or polymeric extrusion in a relatively rigid embodiment, or an inner spring coil tubular element in a relatively flexible embodiment. In either construction, the actuator shaft contains a central lumen such as for receiving an axially moveable core wire.

Figure 9:
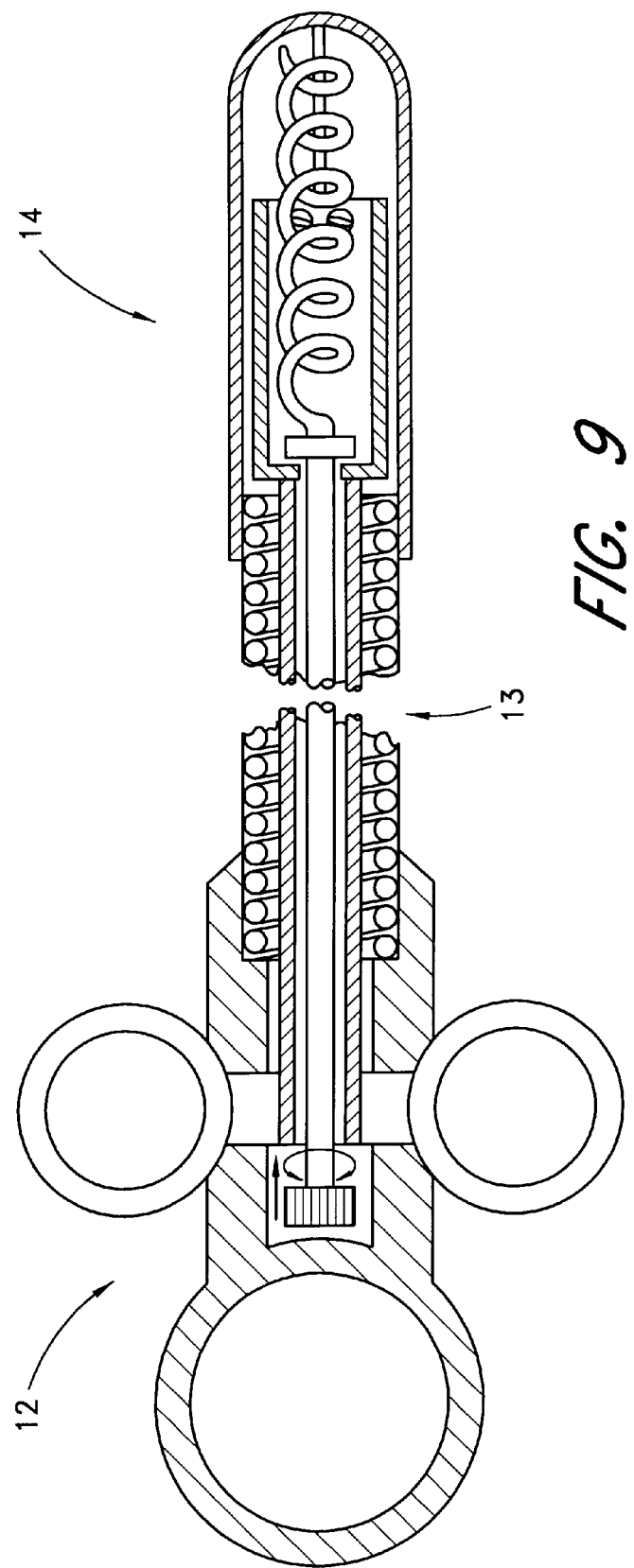
FIG. 9 is an embodiment like that of FIG. 8, with a tissue auger in the central lumen.

The core wire in the embodiment of FIG. 8 accomplishes two functions, either one of which can be utilized without the other. For example, the core wire is provided with a distal harpoon or needle tip for skewering tissue samples which have been severed by the cutting tip. The harpoon can be useful in helping maintain the sequential order of the samples, as well as controlling, handling of the samples following removal from the patient. Modifications of the present embodiment include the use of an auger as illustrated in FIG. 9, which may be rotated such as through the manual manipulation of an auger knob at or about the proximal handle to pull tissue within the tissue collection chamber. Any of a variety of tissue augers and/or harpoons may be readily incorporated into the sample device of the present invention, such as those disclosed in U.S. Pat. No. 5,562,102 to Taylor, the disclosure of which is incorporated in its entirety herein by reference.

As an independent feature of the embodiment of FIG. 8, the core wire is provided with a distal stop 67. As illustrated, the distal stop 67 resides at a proximal end of the sample collection chamber, and is axially movable within the cylindrical wall 72. Distal advancement of the core wire causes the stop 67 to advance distally, thereby expelling the contents of the sample collection chamber. Distal advancement may be accomplished through any of a variety of structures at or about the handle 12, such as levers, slider switches or the like. In the embodiment illustrated in FIG. 9, the auger knob performs a dual function of rotation to advance tissue along the auger, as well as axial displacement to advance the auger and stop distally from the sample collection chamber.

Figure 10:
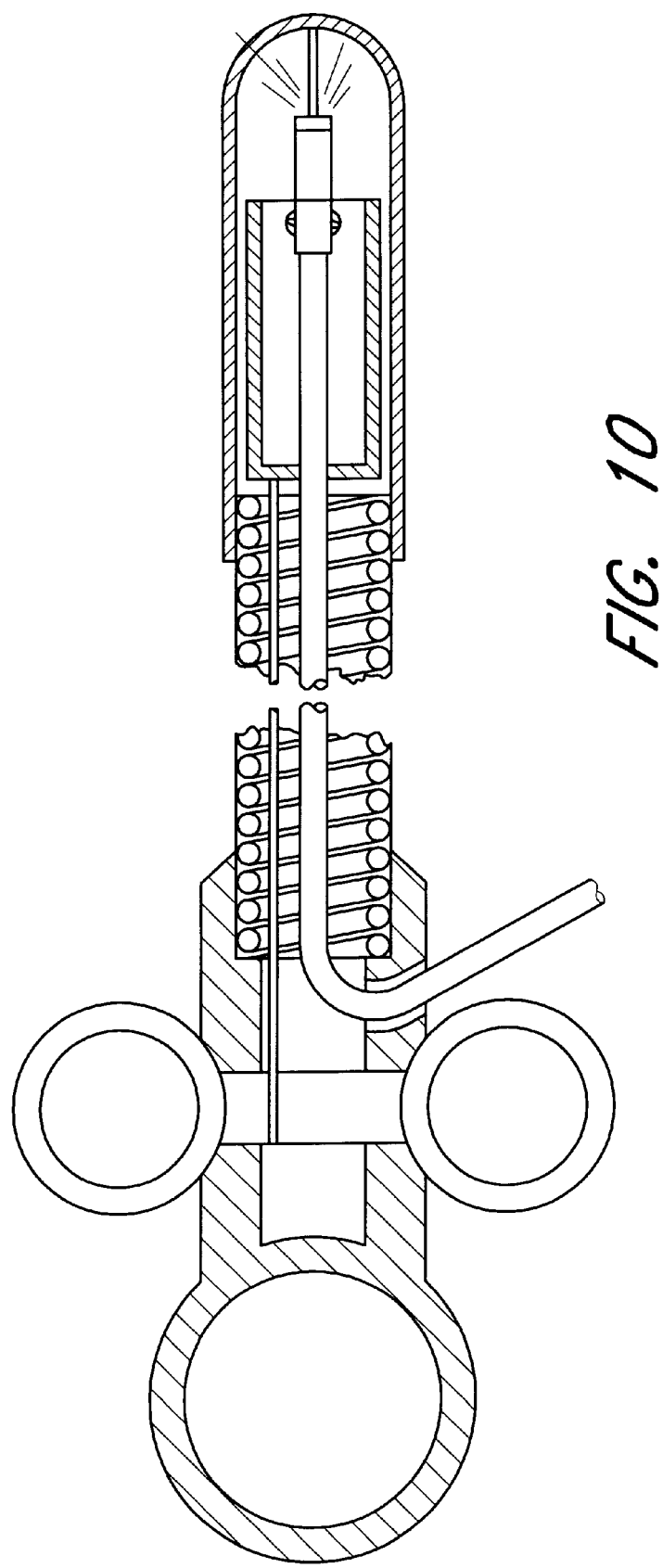
FIG. 10 is a cross-sectional side elevational view of an alternate flexible shaft embodiment of the present invention.

FIGS. 10 and 11 illustrate cross-sectional side elevational views of alternate embodiments of the present invention, adapted for accommodating structures and functions in addition to biopsy sampling. For example, referring to FIG. 10, the push/pull wire in a flexible shaft embodiment is radially offset from the axial center of the shaft, thereby optimizing the cross-sectional area of an elongate central lumen extending throughout the length of the flexible shaft. An aperture is provided in the proximal wall of the sample collection chamber, to provide communication between the sample collection chamber and the central lumen. An access port is provided on the proximal handle, so that an instrument may be introduced through the access port, throughout the length of the central lumen, and into or beyond the sample collection chamber. In one embodiment, the auxiliary lumen is utilized to accommodate a fiber optic bundle to illuminate or visualize the working site. Any of a wide variety of alternative instruments may be advanced through the central lumen as will be apparent to those of skill in the art in view of the disclosure herein.

In the relatively rigid shaft embodiment of FIG. 11, the elongate central lumen which extends through the inner actuator element is provided with an open proximal end. The open proximal end provides direct communication between the proximal end of the device and the distal end of the device, such as for the introduction of auxiliary instruments, sampling devices and the like. In addition, in either of the foregoing embodiments, the auxiliary lumen may be utilized for infusion of fluids with or without medication, as well as the aspiration of fluids. Biopsy samples may similarly be retracted throughout the length of the axial lumen if desired for a particular application.

While the present invention has been described in the context of embodiments of a multiple sample biopsy device 10, it is contemplated that aspects and advantages of the inventive configuration of the present invention can also find utility in other environments of use. For instance, but without limitation, the same concepts can be utilized when forming single bite forceps or other articulating tools, such as electrodes or graspers, for example. The inventive configuration results in lowered production costs and ease of manufacturing and assembly. In addition, the inventive configuration opens the throat region 20 by removing any previously necessary pins or coupling structures which occluded the throat region 20.

It is further contemplated that the sample collection chamber could be extended through the entire device. An embodiment in which the sample collection chamber is coextensive with the medical device could allow for the insertion of another tool from, for instance, the control handle end of the device 10, such as, for example but without limitation, a light fiber or a guide wire. Moreover, the sample collection region 23 could also serve as an open lumen to the control end of the device which would allow the removal of tissue, debris blood, or the like by a use of differential pressure. The application of suction can also be used to aid the intake of samples during a biopsy procedure. Suction can be applied in a number of manners well known to those of skill in the art. For instance, wall suction in the operating room may be connected to the device or the device may be fitted with a simple plunger which will create a vacuum as the plunger is withdrawn either incrementally or steadily through the lumen 22.

Moreover, a removable tissue collection device or plunger could also be incorporated into the device to facilitate the orderly removal of the multiple samples so as to not disturb their sequence. This orderly removal would allow better data collecting abilities because the tissue samples could be better tracked to their origin in the patient's body.

Although the invention has been described in terms of a certain embodiment, other embodiments apparent to those of ordinary skill in the art also are within the scope of this invention. Thus, various changes and modifications may be made without departing from the spirit and scope of the invention. Accordingly, the scope of the invention is intended to be defined only by the claims that follow.

What is claimed is:

1. A multiple sample biopsy device, comprising:
    an elongate body, having a proximal end, a distal end, and an open inner lumen;
    a control on the proximal end of the body; and
    an articulating tip on the distal end of the body;
        the articulating tip comprising a tubular housing, said tubular housing having a slit extending in a proximal direction from a closed distal end thereof, said slit dividing the tubular housing into first and second opposing jaws, the jaws being adapted to move into a least an open and a closed configuration;
        the jaws delimiting an interior space when the jaws are in the closed configuration; and
        the space being in communication with the open inner lumen.

2. A multiple sample biopsy device as in claim 1, wherein the body comprises an elongate flexible tubular body.

3. A multiple sample biopsy device as in claim 2, wherein the body comprises an elongate flexible tubular spring coil.

4. A multiple sample biopsy device as in claim 1, wherein the body comprises a relatively rigid tubular body.

5. A multiple sample biopsy device as in claim 1, wherein the body comprises an elongate tubular body, and further comprising an actuator element axially movably positioned within the tubular body and connected to the articulating tip, so that axial displacement of the actuator with respect to the tubular body causes the jaws to move between a first medial position and a second lateral position.

6. A multiple sample biopsy device as in claim 1, further comprising a sample collection chamber in a distal portion of the device.

7. A multiple sample biopsy device as in claim 6, wherein the sample collection chamber is defined within a tubular housing, said housing axially movably positioned within the articulating tip.

8. A multiple sample biopsy device as in claim 7, further comprising an actuator element extending axially through the body and connecting to the tubular housing defining the sample collection chamber.

9. A multiple sample biopsy device as in claim 8, wherein the actuator comprises a solid rod.

10. A multiple sample biopsy device as in claim 8, wherein the actuator comprises a tubular element.

11. A multiple sample biopsy device as in claim 6, wherein the sample collection chamber further comprises a sample ejector.

12. A multiple sample biopsy device as in claim 11, wherein the sample ejector comprises a moveable wall positioned in the sample collection chamber.

13. A multiple sample biopsy device as in claim 1, further comprising an elongate central lumen extending axially through the body for permitting communication between the proximal control and the tip.

14. A multiple sample biopsy device as in claim 1, further comprising a tissue piercing element contained within the articulating tip.

15. A multiple sample biopsy device as in claim 14, wherein the tissue piercing element is axially movably positioned within the tip.

16. A multiple sample biopsy device as in claim 14, wherein the tissue piercing element comprises a helical coil.

17. A multiple sample biopsy device as in claim 1, wherein each of the first and second jaws is provided with a limit surface on a proximal portion thereof, for contacting the outer surface of the tip to limit lateral rotation of the jaws.

18. A multiple sample biopsy device as in claim 1, wherein each of the first and second opposing jaws is connected to the tubular housing by a flexual element.

19. A cutter tip for mounting on the distal end of a biopsy device, the tip comprising:
    a tubular housing having a proximal end and a closed distal end, the distal end of the tubular housing axially bisected into first and second jaw portions by a proximally extending cut therethrough;
    a tubular sample collection container axially movably positioned within the housing; and
    a moveable connection between the tubular sample container and the first and second jaws such that axial displacement of the tubular sample collection container in a first direction causes the first and second jaws to move laterally away from each other, and axial displacement of the tubular sample container in a second axial direction causes the first and second jaws to advance medially towards each other.

20. A cutting tip as in claim 19, wherein each of the first and second jaws further comprises a flexual element extending between the tubular housing and the jaw.

21. A cutting tip as in claim 20, wherein the flexual member is intregally formed with the jaw and tubular housing.

22. A method of making a cutting tip for use in a medical instrument, comprising the steps of:

providing a tube having a closed distal end and an inner lumen;

cutting the tube from the closed distal end in a proximal direction to divide a portion of the tube into first and second opposing jaws, the jaws delimiting an interior space when the jaws are in a closed configuration, and the space being in communication with the inner lumen;

positioning an actuator within the inner lumen of the tube; and connecting a portion of each jaw to the actuator so that axial displacement of the actuator produces lateral movement of at least one of the jaws.

23. A multiple sample biopsy device, comprising:

an elongate body, having a proximal end and a distal end;

a control on the proximal end of the body;

an articulating tip on the distal end of the body;

the articulating tip comprising a tubular housing having first and second opposing jaws integrally formed with the housing; and a sample collection chamber in a distal portion of the device, wherein the sample collection chamber is defined within a tubular housing, said housing axially movably positioned within the articulating tip.

24. A multiple sample biopsy device as in claim 23, wherein the body comprises an elongate flexible tubular body.

25. A multiple sample biopsy device as in claim 24, wherein the body comprises an elongate flexible tubular spring coil.

26. A multiple sample biopsy device as in claim 23, wherein the body comprises a relatively rigid tubular body.

27. A multiple sample biopsy device as in claim 23, wherein the body comprises an elongate tubular body, and further comprising an actuator element axially movably positioned within the tubular body and connected to the articulating tip, so that axial displacement of the actuator with respect to the tubular body causes the jaws to move between a first medial position and a second lateral position.

28. A multiple sample biopsy device as in claim 23, further comprising an actuator element extending axially through the body and connecting to the tubular housing defining the sample collection chamber.

29. A multiple sample biopsy device as in claim 28, wherein the actuator comprises a solid rod.

30. A multiple sample biopsy device as in claim 28, wherein the actuator comprises a tubular element.

31. A multiple sample biopsy device as in claims 23, further comprising an elongate central lumen extending axially through the body for permitting communication between the proximal control and the tip.

32. A multiple sample biopsy device as in claim 23, further comprising a tissue piercing element contained within the articulating tip.

33. A multiple sample biopsy device as in claim 32, wherein the tissue piercing element is axially movably positioned within the tip.

34. A multiple sample biopsy device as in claim 32, wherein the tissue piercing element comprises a helical coil.

35. A multiple sample biopsy device as in claim 23, wherein the sample collection chamber further comprises a sample ejector.

36. A multiple sample biopsy devices as in claim 35, wherein the sample ejector comprises a moveable wall positioned in the sample collection chamber.

37. A multiple sample biopsy devices as in claim 23, wherein each of the first and second jaws is provided with a limit surface on a proximal portion thereof, for contacting the outer surface of the tip to limit lateral rotation of the jaws.

38. A multiple sample biopsy device as in claim 23, wherein each of the first and second opposing jaws is connected to the tubular housing by a flexual element.

* * * * *